US008871183B2

(12) United States Patent
Clarot et al.

(10) Patent No.: US 8,871,183 B2
(45) Date of Patent: *Oct. 28, 2014

(54) COMPOSITION FOR PROMOTING AND MAINTAINING ORAL HEALTH

(75) Inventors: Tim Clarot, Phoenix, AZ (US); Regina Miskewitz, Phoenix, AZ (US)

(73) Assignee: Zicare, LLC, Scottsdale, AZ (US)

( * ) Notice: Subject to any disclaimer, the term of this patent is extended or adjusted under 35 U.S.C. 154(b) by 1610 days.

This patent is subject to a terminal disclaimer.

(21) Appl. No.: 11/749,111

(22) Filed: May 15, 2007

(65) Prior Publication Data

US 2007/0292371 A1 Dec. 20, 2007

Related U.S. Application Data

(60) Provisional application No. 60/800,638, filed on May 15, 2006, provisional application No. 60/800,639, filed on May 15, 2006, provisional application No. 60/800,636, filed on May 15, 2006.

(51) Int. Cl.
| | |
|---|---|
| *A61K 8/00* | (2006.01) |
| *A61K 8/27* | (2006.01) |
| *A61K 33/30* | (2006.01) |
| *A61K 31/14* | (2006.01) |
| *A61Q 11/00* | (2006.01) |
| *A61K 8/49* | (2006.01) |
| *A61K 31/44* | (2006.01) |

(52) U.S. Cl.
CPC .............. *A61K 8/4926* (2013.01); *A61Q 11/00* (2013.01); *A61K 8/27* (2013.01); *A61K 31/44* (2013.01)
USPC ................. 424/49; 424/401; 424/54; 424/641

(58) Field of Classification Search
USPC ...................... 424/49, 54, 401, 641
See application file for complete search history.

(56) References Cited

U.S. PATENT DOCUMENTS

| | | | |
|---|---|---|---|
| 4,242,323 A | 12/1980 | Vlock | |
| 4,335,002 A * | 6/1982 | Mussinan et al. | ................. 252/1 |
| 4,664,906 A | 5/1987 | Sipos | |
| 4,773,548 A | 9/1988 | Deussen | |
| 5,578,295 A | 11/1996 | Francis et al. | |
| 5,855,873 A * | 1/1999 | Yam | ................................. 424/49 |
| 5,948,390 A | 9/1999 | Nelson et al. | |
| 6,121,315 A * | 9/2000 | Nair et al. | ..................... 514/494 |
| 6,355,229 B1 | 3/2002 | Adamy | |
| 2003/0003059 A1 | 1/2003 | Dana | |
| 2003/0091514 A1* | 5/2003 | Stier | ............................... 424/48 |
| 2004/0037789 A1* | 2/2004 | Moneuze et al. | ............... 424/49 |
| 2004/0131559 A1 | 7/2004 | Hauck | |
| 2005/0026107 A1 | 2/2005 | Montgomery | |

FOREIGN PATENT DOCUMENTS

| | | |
|---|---|---|
| GB | 2210264 A | 6/1989 |
| WO | 9015592 A | 12/1990 |
| WO | 9639995 A | 12/1996 |
| WO | 03075865 | 9/2003 |
| WO | 2004071321 | 8/2004 |

OTHER PUBLICATIONS

University of Iowa Health Science Relations, Saliva: It Protects Our Mouth, Jun. 2003, www.uihealthcare.com/topics/medicaldepartments/dentistry/saliva/index.html.
Anonymous, "The Importance of Oral Hygiene," Product Presentation for C.E.T. Rinses and Gels, http://web.archive.org/web/20050207022050/http://www.virbac.co.nz/ArticleDisplay.asp?item=68>, Feb. 7, 2005.
Anonymous, "Rinsing Product," C.E.T. Home Dental Care, http://web.archive.org/web/20060211005349/http://www.cetdental.com/rinsing_products.asp>, Feb. 11, 2006.
Schiff, Thomas, "Anticalculus effect of a cetylpyridinium chloride/zinc gluconate mucoadhesive gel: results of a randomized, double-blind, controlled clinical trial." The Journal of Clinical Dentistry, Oct. 2007.
Fortune, Bruce, International Search Report and Written Opinion dated Nov. 7, 2007.
Simon, Frederic, International Search Report and Written Opinion dated Nov. 23, 2007.

\* cited by examiner

*Primary Examiner* — Lezah Roberts
(74) *Attorney, Agent, or Firm* — Snell & Wilmer L.L.P.

(57) ABSTRACT

A composition for improving oral health and methods of using and forming the composition are disclosed. The composition includes one or more active ingredients and a carrier. The composition is configured to maintain the active ingredient(s) with a surface of an oral cavity for an extended period of time to promote oral health and hygiene.

20 Claims, No Drawings

COMPOSITION FOR PROMOTING AND MAINTAINING ORAL HEALTH

CROSS REFERENCE TO RELATED APPLICATIONS

This application claims the benefit of U.S. Patent Application Ser. No. 60/800,638, entitled METHOD AND SYSTEM FOR FACILITATING ORAL HEALTH, filed May 15, 2006; Ser. No. 60/800,639, entitled ORAL CARE PROTECTION SYSTEM, filed May 15, 2006; and Ser. No. 60/800,636, entitled ORAL CARE GEL COMPOSITION FOR IMPROVING OR MAINTAINING ORAL HEALTH, filed May 15, 2006.

FIELD OF INVENTION

The present invention generally relates to compositions for promoting and maintaining oral health and hygiene. More particularly, the invention relates to a composition for facilitating oral health, such as through the reduction and/or prevention of tartar, plaque, gingivitis, and other oral diseases.

BACKGROUND OF THE INVENTION

Unfortunately, poor oral health affects millions of people every year. Poor oral health may result in symptoms ranging from bad breath, tooth decay, and tooth coloration, to more serious health problems, such as gum disease, tooth loss, and even general health problems, such as heart disease, stroke, poorly controlled diabetes and preterm labor.

The presence of dental plaque, or simply plaque, in an oral cavity can lead to such oral and general health problems. Plaque can be defined as an organized, coherent, gel-like or mucoid material that includes microorganisms in an organic matrix derived from saliva and extracellular bacterial products such as glucans, fructans, enzymes, toxins, and acids. Plaque may also contain other cells, such as desquamated epithelial cells, and inorganic components, such as calcium and phosphate. In general, dental plaque is a bacterial accumulation. Generally transparent and sticky, plaque accumulates around the teeth at the cervical margin, and then grows apically.

Once plaque forms on a surface, the plaque resists removal, and usually can be removed only by mechanical means, such as, for example, by brushing and flossing the affected areas. If not removed, however, the presence of plaque can give rise to tartar formation, tooth decay, gingivitis, periodontitis, and other health problems.

Tartar is a hard, calcified plaque material that exhibits a yellowish or brownish color. Tartar forms as a result of minerals (e.g., those present in saliva and gum pockets) reacting with plaque material to form a rough calculus. Calculus generally arises from the nucleation of calcium phosphate, often in areas where the large salivary gland ducts secrete their saliva. As such, calculus can form on surfaces not covered by the oral mucosa (supragingival) or on surface located apical to the soft tissue margin of the gingiva (subgingival).

Tartar adheres to hard surfaces such as enamel, roots, and dental devices, such as dentures, bridges, crowns, and the like, and is generally more difficult to remove than plaque. Brushing and flossing are normally not sufficient to remove tartar from a surface.

If left untreated, tartar buildup can be problematic in several regards. For example, the rough, porous surface of tartar serves as a breeding ground for additional bacteria, which can calcify and form additional tartar. The bacteria growth can, in turn, lead to tooth decay, gum disease, tooth loss, as well as systemic health problems.

In addition to the health concerns, tartar is a cosmetic problem due to its discoloration of teeth. Namely, teeth can become a yellowish or brownish color. Moreover, because the surface of tartar is rough and porous, the tartar absorbs colors from other sources (e.g., coffee, tea, tobacco, smoke, red wine and the like), and thus the presence of tartar exacerbates cosmetic tooth coloration typically associated with such other sources.

Typical methods of preventing tartar buildup include brushing with tartar-control toothpaste. Although such toothpastes, if used regularly, may prevent additional buildup of tartar, the toothpastes are not thought to be effective at removing existing tartar from tooth and device surfaces.

Methods of removing existing tartar typically include scaling or root planing, both of which are performed by dentists or hygienists with the aid of specialized tools. Although these techniques work well, they are relatively expensive and time consuming. Furthermore, various methods for inhibiting tartar may cause damage to tooth enamel and/or to dental devices.

Accordingly, improved compositions for removing existing tartar and plaque and for reducing an amount of plaque and tartar buildup are desired.

SUMMARY OF THE INVENTION

In accordance with various aspects of the present invention, a composition for promoting and maintaining oral health is provided. The exemplary oral health care composition can be used as a relatively inexpensive and safe treatment for facilitating maintenance and improvement of oral health and/or hygiene, such as through the prevention and/or reduction of tartar, plaque, gingivitis, and other diseases. In addition, the composition is relatively easy to use, does not require a visit to a dentist office, and does not damage the surface of enamel.

In accordance with various exemplary embodiments of the invention, a composition includes at least one active ingredient to promote and/or maintain oral health. In accordance with various aspects of this embodiment, the composition is designed to maintain the active ingredient(s) in contact with a surface for an extended period of time. Exemplary compositions have a viscosity greater than about 20,000 centipoise (cp), preferably greater than about 30,000 cp, and more preferably greater than about 35,000 cp. The viscosity of the compositions may range from about 20,000 to about 250,000 cp, about 25,000 to about 100,000 cp, or about 30,000 to about 50,000 cp. Suitable active ingredients include cetylpyridinium chloride (CPC), zinc salts, other antimicrobial agents, and other ingredients to improve oral health.

In accordance with other embodiments of the invention, a composition includes a plurality of active ingredients to improve oral health. In accordance with various aspects of this embodiment of the invention, the composition includes a carrier having a thickening agent, wherein the composition is configured to maintain the plurality of active ingredients in contact with a surface for an extended period of time. Exemplary thickening agents suitable for use in the composition include hydroxyethylcellulose and other pharmaceutically acceptable thickeners, and exemplary active ingredients include CPC, zinc salts, other antimicrobial agents, and similar agents known to reduce or prevent buildup of tartar, plaque gingivitis, gum bleeding, periodontitis, or other disease and/or the effects of the same.

In accordance with further embodiments of the invention, a composition includes one or more active ingredients to improve oral health and a carrier including a thickening agent. Exemplary thickening agents suitable for use in the composition include hydroxyethylcellulose, glycerin, and other pharmaceutically acceptable thickeners, and exemplary active ingredients include CPC, zinc salts, other antimicrobial agents, and similar agents known to improve oral health.

DETAILED DESCRIPTION

The present invention provides a composition to improve oral health. The composition can be used to improve oral health of various animals, and is particularly well suited for the treatment of humans by applying the composition to a surface within an oral cavity.

As used throughout this application, the term "surface" includes any surface on which plaque, tartar, or gum disease may form. Exemplary surfaces include teeth (both supragingival and subgingival), gums, and dental devices such as bridges, crowns, fillings, braces, and the like. Further, as used herein, the term "measurably improve" means a measurable difference between an amount measured without use of the composition or system of the present invention and with or after use of the system. The measurements may be compared for the same surface (before and after) or between test and control groups.

A dose size of the composition may vary in accordance with several factors, such as the particular ingredients, the dilution of the composition, and the like. Exemplary dose sizes for purpose of illustration range from about 1 mg to about 6 mg, preferably about 2 mg to about 5 mg, and more preferably about 3 mg to about 4 mg.

In accordance with various exemplary embodiments, a composition includes an active ingredient and a viscous carrier. In this case, the composition is configured to maintain the active ingredient in contact with a surface of an oral cavity for an extended period of time to allow the active ingredient(s) to remain in contact with the surface for an extended period.

Exemplary active ingredients suitable for use with systems of the invention include one or more of the following: cetylpyridinium chloride (CPC), dicalcium phosphate dehydrate, hydrogen peroxide, sanguinaria extract, sodium bicarbonate, sodium lauryl sulfate, sodium fluoride, stannous fluoride, sodium monofluorophosphate (MFP), zinc salts such as zinc chloride, zinc acetate, zinc citrate, zinc oxide and zinc gluconate, alkyl dimethyl amine oxide, alkyl dimethyl glycine, eucalyptol, menthol, methyl salicylate, thymol, sodium citrate, peppermint oil, sage oil, polymethylsiloxane, polxamer, and stannous pyrophosphate. Other now known or hereafter devised actives may also be used. For example, any agent, which alone or in combination is able to prevent or alleviate the severity of problems associated with dentition may be utilized. Such may include anti-caries agents and the like; agents useful in reducing tooth hypersensitivity, such as potassium nitrate, strontium chloride and/or the like; and/or plaque and calculus reducing agents, such as, for example, chlorhexidine, quaternary ammonium compounds (e.g. benzethonium chloride, domphen bromide, etc.), triclosan, herbal compounds (e.g. sanguinarine), stannous salts, complex phosphates (e.g., pyrophosphates), SLS (e.g. sodium lauryl sulfate), hydrogen peroxide, and/or the like.

An amount of the active ingredient for use with composition in accordance with various embodiments of the invention varies in accordance with the dosage size and particular ingredient(s). In general, the active or actives selected will be used in a suitably effective amount, generally on the order of less than about 10 wt %, and more preferably 5 wt % or less. In a particularly preferred composition, the active ingredient is present in an amount of about 0.001 wt % to about 1.5 wt %, within an amount of about 0.025 wt % to about 1.0 wt %, or even within an amount about 0.05 wt % to about 0.7 wt %. All percentages set forth herein are in weight percent of the total composition, unless otherwise indicated.

In accordance with one preferred exemplary embodiment, the active ingredient(s) include CPC. In one case, CPC is present in an amount of about 0.001% to about 1%, in an amount of about 0.01% to about 0.5%, or even in an amount of about 0.05% to about 0.25% or about 0.045% to about 0.1%. In accordance with another exemplary embodiment, the active ingredient(s) also include zinc gluconate. In one case, zinc gluconate is present in an amount of about 0.001% to about 2%, in an amount of about 0.01% to about 1.5%, or even in an amount of about 0.05% to about 1.25%.

In accordance with an exemplary embodiment, the composition also includes a thickener to obtain the desired viscosity. Suitable thickening agents include substances which increase the viscosity of the composition, cause the composition to gel or coagulate, or the like, such as food-grade or pharmaceutical-grade thickeners, including, for example, hydroxyethylcellulose, hydroxypropyl methylcellulose, carrageenan, guar gum, methylcellulose, methyethylecellulose, acceptable non-ionic thickeners, and the like. The thickener may be present in an amount of about 0.01% to about 10%, in an amount of about 0.1% to about 7%, or even in an amount of about 1% to about 5% or about 0.5% to about 3%.

The composition may also include a humectant such a glycerin, which may be present in an amount of about 0.01% to about 15%, preferably about 0.1% to about 10%, and more preferably about 1% to about 7%. When used, the humectant may facilitate maintaining the composition in a liquid form and may help maintain a desired viscosity. In accordance with specific aspects, glycerin facilitates maintaining one or more of the active ingredients in an ionic form and/or facilitates the transport of the active ingredients through the composition.

The composition may also include a diluent. Exemplary diluents suitable for use with the present composition include sorbitol, xylitol, mannitol, water, alcohols, and oils. In accordance with particular examples of the invention, the composition includes purified water in an amount of about 80% to about 99%, preferably about 85% to about 95%, and more preferably about 88% to about 92%.

The composition may also include sugar alcohols such as sorbitol and xylitol, monnital, lactitol, and the like that act as a sweetener and also as a humectant and/or emulsifier and/or diluent. When used, sorbitol or other sugar alcohol can be present in an amount of about 0.001% to about 0.5%, in an amount of about 0.01% to about 0.1%, or even in an amount of about 0.025% to about 0.075%. Compositions in accordance with the invention may alternatively include a greater percentage of sugar alcohol(s).

The composition may also include a natural or artificial sweetener such as cyclamates, sucralose, saccharin (e.g., sodium or calcium), ace-k, or aspartame which, when included in the composition, can be present in an amount of about 0.001% to about 1.5%, in an amount of about 0.01% to about 1%, or even in an amount of about 0.25% to about 0.75%.

Colorants may also be added to the composition. For example, the composition can include colorants, such that when the composition is applied to or proximate the gingiva, the composition has a color indicative of healthy gingiva—e.g., the composition can be pink in color. Such a composition having a color indicative of healthy gingiva can provide added incentive to users to continue using the composition, which in turn promotes improved health care and hygiene. Colorants may be present in any desired amount. For example, the colorants may include Red #33 and/or Red #40, available from Pylam in an amount of about 0.000005% to about 1%, preferably about 0.00050% to about 0.5%, and more preferably about 0.001% to about 0.1%. Additionally or alternatively, colorants, which are indicative of flavor may be added to the composition. Examples include FD&C Blue #1, D&C Green #5, FD&C Yellow #5, and FD&C Yellow #6.

The composition may also include flavorants such as cinnamon oil, clove oil, mints, anise, citrus, fruits, and the like, which, when included in the formula, are present in an amount of about 0.01% to about 2%, in an amount of about 0.01% to about 1%, or even in an amount about of about 0.1% to about 0.5%.

Essential oils such as cinnamon bark oil and clove bud oil may be particularly advantageous because they exhibit additional desirable qualities. For example, cinnamon bark oil exhibits antibacterial, antiseptic, antiviral, antispasmodic, antifungal, sedative and analgesic properties and clove bud oil has local anesthetic, antiseptic, antibacterial, and stimulating properties.

The composition is configured to maintain contact with an oral cavity surface for an extended period of time, which has several advantages over traditional compositions. The composition preferably exhibits good microadhesion, and moreover, the composition preferably is quite viscous. As such, in general, relatively small amounts of the composition and consequently the active agent(s) can be used to effectively provide oral health care or treatment. Additionally, the relatively high viscosity allows for relatively select placement of the composition on a surface.

The composition may have a viscosity greater than about 20,000 cp, preferably greater than 30,000 cp, and more preferably greater than about 35,000 cp. By way of more particular examples, the viscosity of the composition ranges from about 20,000 cp to about 250,000 cp, preferably about 25,000 cp to about 100,000 cp, and more preferably about 30,000 cp to about 50,000 cp, and yet more preferably about 35,000 cp to about 45,000 cp. The viscosity values as set forth herein are measured using a Brookfield, Model DV-II+ Pro viscometer, spindle #6, 10 RPM for 90 seconds at 25 C.

In accordance with other exemplary embodiments, the composition includes multiple active ingredients in a carrier. For example, the composition can include a plurality of any active ingredients and a carrier in the weight percents disclosed herein. The composition may also include any of the optional ingredients, such as thickeners, sweeteners, flavorants, and colorants as set forth herein. For example, in accordance with an exemplary embodiment, the composition includes CPC and zinc gluconate as the active ingredients, wherein the CPC is present in an amount of about 0.001% to about 1%, in an amount of about 0.01% to about 0.5%, or even in an amount of about 0.05% to about 0.25% or about 0.045% to about 0.1%; and wherein the zinc gluconate is present in an amount of about 0.001% to about 1.5%, in an amount of about 0.01% to about 1.0%, or even in an amount of about 0.05% to about 0.75%.

In accordance with other exemplary embodiments, the composition includes one or more active ingredients and a colorant indicative of healthy gingival, wherein the color of the composition is more than merely decorative; it also serves the function of encouraging those that use the product to continue to use the product because there is an immediate appearance, upon application of the composition, that healthy gingival is achieved.

A pH of the composition may vary in accordance with a particular application. In accordance with various embodiments of the invention, the pH is between about 4-10, preferably about 4-7, and more preferably about 5-5.4.

A method of forming a composition in accordance with various embodiments of the invention includes the steps of adding a humectant (e.g., glycerin) to a first mixing vessel and the adding a thickener (e.g., hydroxyethylcellulose) to the humectant and mixing until a uniform, lump-free slurry forms. The slurry should not sit for too long at this stage, or it may become cement-like in texture and viscosity. In a second mixing vessel, add a diluent (e.g., water) and add the humectant/thickener slurry slowly (over a period of a few hours) to the diluent and mix until a smooth mixture is obtained. Once the gum is hydrated, add any sugar alcohol, sweetener, and colorant to the mixture and mix until each is dissolved. Finally, add the actives and any oils and mix until the actives and oils are dispersed in the solution.

SPECIFIC EXAMPLES

The following non-limiting examples illustrate improvement in oral health using a system, kit, and method in accordance with various embodiments of the invention. These examples are merely illustrative, and it is not intended that the invention be limited to the examples. Systems in accordance with the present invention may include the ingredients listed below as well as additional and/or alternative inert materials, preservatives, and other constituents typically found in compositions for promoting oral health. In the case where exemplary inert materials and/or preservatives are listed, these ingredients are merely exemplary, and it is understood that other similar ingredients may be substituted for the materials listed in the examples below.

Example 1

A pale light pink viscous gel, having a viscosity of about 40,000 cp, with cinnamon-clove characteristic odor and taste is formed by admixing the following ingredients, as described above, in the amounts shown.

TABLE 1

| Ingredient | Supplier | Weight % | Exemplary Wt % Range |
|---|---|---|---|
| Purified Water | Copacker | 91.504 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Cetylpyridinium Chloride | Dishman Pharmaceuticals | 0.100 | 0.001-1 |
| Zinc Gluconate USP | American International | 0.592 | 0.001-1.5 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

A clinical study, including 24 subjects, evaluating the efficacy of the composition of Table 1 was conducted. Subjects were scored at baseline, three weeks, and at six weeks using the Low and Silness Gingival Index (1963) (GI) and the Turesky Modification (1970) of the Quigley Hein Plaque Index (1962) (PI) indices. Plaque and calculus quality, thickness, maturity, and mass were also observed at these times.

At the end of a three-week period, there was an observed lessening or reduction of plaque quality, thickness, mass, and maturity; the lessening was greater (greater decrease) for those using the composition of Table 1, compared to a placebo. The observance that plaque quality was reduced is important because the presence of actively growing plaque bacteria (biofilm) is important in the development of inflammation, which leads to gingivitis and periodontitis.

In addition, at the end of the three-week period, a lessening of the quality of calculus was also observed. A general improvement of gingival health was also observed. An extremely thin, slightly detached layer of epithelial cells was also found on the surface of attached gingival surfaces at the marginal ridge, close to the areas where plaque and tartar was likely disrupted off the teeth with subjects using the composition of Table 1, which indicated promotion of faster healing of gingival tissues.

Subjects at the end of the six-week period showed a statistically significant (p-value=0.05) greater performance than a placebo in both absolute (0.741) and percentage (40%) improvement in GI. There was also a directional improvement for PI in the absolute (1.805) and percent (49%) improvement for those using the formula of Table 1 compared to a placebo. There was also approximately a 50% reduction in plaque thickness at the end of the six-week period in about 73% of the subjects that were checked for plaque quality or thickness.

Example 2

A pale light pink viscous gel, having a viscosity of about 40,000 cp, with cinnamon-clove characteristic odor and taste is formed by admixing the following ingredients, as described above, in the amounts shown.

TABLE 2

| Ingredient | Supplier | Weight % | Exemplary Wt % Range |
|---|---|---|---|
| Purified Water | Copacker | 92.096 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Cetylpyridinium Chloride | Dishman Pharmaceuticals | 0.100 | 0.001-1 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

A clinical study, including 22 subjects, evaluating the efficacy of the composition of Example 2 was conducted. The Low and Silness Gingival Index (1963) (GI) for subjects using the formula of Table 2 for a six-week period showed a greater performance than a placebo in both absolute (0.405) and percentage (22%) improvement in GI. There was also a directional improvement for the Turesky Modification (1970) of the Quigley Hein Plaque Index (1962) (PI) in the absolute (1.489) and percent (41%) improvement for those using the formula of Table 2 compared to a placebo.

Example 3

A clinical study comparing V-MI scores of subjects using the composition of Table 1 was conducted to evaluate calculus dissolution. During the three-month study, the subjects were instructed to brush with toothpaste twice daily and apply the composition prior to retiring. The subjects did not receive a professional cleaning just prior to the study, which evaluated the efficacy of the composition to remove tartar.

For 18 subjects using a system including the composition of Table 1, there was a statistically significant difference between original V-MI scores and V-MI scores (51%) after three months of treatment with the product, which indicates the system is effective at calculus dissolution.

Example 4

In another clinical study, 50 subjects received professional prophylaxis, including scaling and polishing, to remove supragingival calculus, extrinsic stain, and plaque deposits from the mandibular anterior teeth and initial V-MI measurements at 18 VM sites per subject were recorded prior to the study to evaluate calculus inhibition. Subjects were requested to refrain from flossing the mandibular 6 anterior teeth and place the composition between and around those teeth. At the end of a three-month period, VM-I measurements for the same teeth were recorded and analyzed using analysis of covariance. The V-MI scores at the end of the three-month period were statistically significantly lower (59%) than the initial V-MI scores. The study indicated that the system was effective at calculus inhibition.

Example 5

A clinical study comparing V-MI scores of 40 subjects using the composition of Table 1 was conducted to evaluate disruption or dissolution of existing calculus bridges. During a three-month study, the subjects were instructed to brush with toothpaste twice daily and apply the composition prior to retiring.

At the end of the three-month study, a statistically significant difference (30% difference) of before and after scores of the subjects using the composition of Table 1 was observed. In addition, a statistically significant difference (26% difference) of the 40 subjects compared to 40 subjects using a placebo was observed, and a statistically significant difference (99%) between the change in scores before and after the study between the placebo group and the group using a system including the composition of Table 1.

Example 6

A clinical study comparing Gingivitis Index (GI), Plaque Index (PI), and Bleeding Index (BI) scores using the composition of Table 1 was conducted. Forty-five subjects were evaluated over a period of three months and 39 subjects were evaluated over a period of six months. During the study, the subjects were instructed to brush with toothpaste twice daily and apply the composition prior to retiring. The subjects were asked not to use other oral hygiene products. After a baseline examination, all subjects received dental prophylaxis.

At the end of the three-month period, a 16% reduction in GI was observed, a 26% reduction in PI was observed, and a 68% reduction in BI was observed. At the end of the six-month period, a 32% reduction in GI was observed, a 33% reduction in PI was observed, and a 78% reduction in BI was observed. All reductions are statistically significant (p-Value <0.01) using the Mann-Whitney Rank Sum Test.

Example 7

A pale light pink viscous gel, having a viscosity of about 40,000 cp, with cinnamon-clove characteristic odor and taste is formed by admixing the following ingredients, as described above, in the amounts shown.

TABLE 3

| Ingredient | Supplier | Weight % | Exemplary Wt % Range |
|---|---|---|---|
| Purified Water | Copacker | 91.604 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Zinc Gluconate USP | American International | 0.592 | 0.001-1.5 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

A clinical study comparing Gingivitis Index (GI), Plaque Index (PI), and Bleeding Index (BI) scores using the composition of Table 3 was conducted. Fifty-one subjects were evaluated over a period of three months and forty-three people were evaluated over a period of six months. During the study, the subjects were instructed to brush with toothpaste twice daily and apply the composition prior to retiring. The subjects were asked not to use other oral hygiene products. After a baseline examination, all subjects received dental prophylaxis.

At the end of the three-month period, an 11% reduction in GI was observed, a 17% reduction in PI was observed, and a 58% reduction in BI was observed. At the end of the six-month period a 16% reduction in GI was observed, a 21% reduction in PI was observed, and a 52% reduction in BI was observed. All reductions are statistically significant (p-Value<0.01) using the Mann-Whitney Rank Sum Test.

Example 8

A clinical study comparing Gingivitis Index (GI), Plaque Index (PI), and Bleeding Index (BI) scores using the composition of Table 2 was conducted. Fifty subjects were evaluated over a period of three months and 44 people were evaluated over a period of six months. During the study, the subjects were instructed to brush with toothpaste twice daily and apply the composition prior to retiring. The subjects were asked not to use other oral hygiene products. After a baseline examination, all subjects received dental prophylaxis.

At the end of the three-month period, a 18% reduction in GI was observed, a 25% reduction in PI was observed, and a 65% reduction in BI was observed. At the end of the six-month period, a 31% reduction in GI was observed, a 32% reduction in PI was observed, and a 75% reduction in BI was observed. All reductions are statistically significant (p-Value <0.01) using the Mann-Whitney Rank Sum Test.

Example 9

A clinical study comparing V-MI scores using a placebo and the compositions of Tables 1 and 4 was conducted. In this study, 90 subjects were enrolled and 84 completed. Data was recorded at baseline, 40 days and 90 days. Subjects were provided coded tubes of the gel formulation to which they were assigned. The subjects were instructed to apply the gel daily, once before going to bed. The gel was applied between the teeth at the gum margin all along the arch. After applying, the subject was asked to spit out any excess and not to eat or drink prior to the rest period.

TABLE 4

| Ingredient | Supplier | Weight % | Exemplary Wt % Range |
|---|---|---|---|
| Purified Water | Copacker | 91.504 | 80-99 |
| Glycerin USP | Acme-Hardesty | 5.000 | 0.01-15 |
| HEC 250 HX | Hercules-Aqualon | 2.000 | 0.01-10 |
| Sorbitol | Roquette | 0.050 | 0.001-0.5 |
| Sucralose | Tate & Lyle | 0.400 | 0.001-1.5 |
| Cetylpyridinium Chloride | Dishman Pharmaceuticals | 0.100 | 0.001-1 |
| Zinc Gluconate USP | American International | 1.184 | 0.001-1.5 |
| Cinnamon Bark (Oil) | Spectrum | 0.250 | 0.001-2 |
| Clove Bud (Oil) | Spectrum | 0.005 | 0.001-2 |
| Red #40 (1% sol.) | Pylam | 0.099 | 0.000005-1 |

After 90 days, users of the composition of Table 4 had 19% better V-MI scores and users of the composition of Table 1 had 10% better V-MI scores. Moreover, scoring of lingual calculus reduction from intraoral images suggested that the compositions of Tables 1 and 4 were more effective than the placebo. Following treatment, users of the composition of Table 1 had 0.31 better absolute V-MI scores and users of the composition of Table 4 had 0.32 better absolute V-MI scores.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. These and other changes or modifications are intended to be included within the scope of the present invention, as set forth in the following claims.

We claim:

1. A gel composition to improve oral health, the gel composition consisting of:
   about 0.001 weight percent to about 1 weight percent cetylpyridinium chloride;
   about 1 weight percent to about 7 weight percent glycerin;
   about 0.001 weight percent to about 2 weight percent zinc gluconate;
   about 80 weight percent to about 99 weight percent purified water;
   optionally one or more sweeteners;
   one or more flavorants consisting of one or more essential oils;
   optionally one or more colorants; and
   about 0.01 weight percent to about 10 weight percent thickener selected from the group consisting of hydroxyethylcellulose, hydroxypropyl methylcellulose, carrageenan, guar gum, methylcellulose, and methylethylcellulose, wherein the viscosity of the gel composition ranges from about 20,000 centipoise to about 250,000 centipoise as measured at 25° C.

2. The gel composition to improve oral health according to claim 1, wherein the zinc gluconate is about 0.01 weight percent to about 1 weight percent of the gel composition.

3. The gel composition to improve oral health according to claim 1, wherein the thickener selected from the group consisting of hydroxyethylcellulose, hydroxypropylmethylcellulose, carrageenan, guar gum, methylcellulose, and methylethylcellulose is about 1 weight percent to about 5 weight percent of the gel composition.

4. The gel composition to improve oral health according to claim 1, wherein a viscosity of the gel composition is about 35,000 to about 45,000 centipoise as measured at 25° C.

5. The gel composition to improve oral health according to claim 1, wherein the zinc gluconate is about 0.05 weight percent to about 0.75 weight percent of the gel composition.

6. The gel composition to improve oral health according to claim 1, wherein the one or more sweeteners comprises a sugar alcohol.

7. The gel composition to improve oral health according to claim 1, wherein the one or more colorants comprises a colorant indicative of healthy gingiva.

8. The gel composition to improve oral health according to claim 1, wherein the viscosity of the composition is about 25,000 cp to about 100,000 cp as measured at 25° C.

9. The gel composition to improve oral health according to claim 1, wherein the viscosity of the gel composition is about 30,000 cp to about 50,000 cp as measured at 25° C.

10. The gel composition to improve oral health according to claim 1, are wherein the one or more flavorants are a plurality of essential oils.

11. The gel composition to improve oral health according to claim 1, wherein the one or more essential oils comprise cinnamon bark oil.

12. The gel composition to improve oral health according to claim 1, wherein the one or more essential oils comprise clove bud oil.

13. The gel composition to improve oral health according to claim 10, wherein the cetylpyridinium chloride is about 0.01 weight percent to about 0.5 weight percent of the gel composition.

14. The gel composition to improve oral health according to claim 1, wherein a pH of the gel composition is about 5 to about 5.4.

15. A gel composition for maintaining and improving oral health, the gel composition consisting of:
    about 0.001 weight percent to about 1 weight percent cetylpyridinium chloride;
    about 0.001 weight percent to about 2 weight percent zinc gluconate;
    about 1 weight percent to about 7 weight percent glycerin;
    optionally one or more sweeteners;
    one or more flavorants consisting of one or more essential oils;
    optionally one or more colorants;
    a thickener selected from the group consisting of hydroxyethylcellulose, hydroxypropyl methylcellulose, carrageenan, guar gum, methylethylcellulose, and methyethylecellulose; and
    about 80 weight percent to about 99 weight percent purified water;
    wherein the gel composition has a viscosity greater than about 20,000 cp and less than about 250,000 cp, measured at 25° C.

16. The gel composition for maintaining and improving oral health of claim 15, wherein the viscosity is about 25,000 cp to about 100,000 cp, measured at 25° C.

17. The gel composition for maintaining and improving oral health of claim 15, wherein the viscosity is about 30,000 cp to about 50,000 cp, measured at 25° C.

18. A gel composition for maintaining and improving oral health, the gel composition consisting of:
    about 0.001 weight percent to about 1 weight percent of cetylpyridinium chloride;
    a about 0.001 weight percent to about 2 weight percent of zinc gluconate;
    about 80 weight percent to about 99 weight percent purified water;
    a thickener;
    about 1 weight percent to about 7 weight percent humectant;
    a sugar alcohol;
    a sweetener;
    a flavorant consisting of one or more essential oils; and
    a colorant,
    wherein the gel composition has a viscosity greater than about 20,000 cp and less than about 250,000 cp, measured at 25° C.

19. The gel composition for maintaining and improving oral health of claim 18, wherein the flavorant is a plurality of essential oils.

20. The gel composition for maintaining and improving oral health of claim 18, wherein the colorant is indicative of healthy gingival.

* * * * *